United States Patent
Pütter et al.

(10) Patent No.: US 11,491,317 B2
(45) Date of Patent: Nov. 8, 2022

(54) CONNECTOR ASSEMBLY FOR CONNECTING MEDICAL LINES TO EACH OTHER

(71) Applicant: Fresenius Kabi Deutschland GmbH, Bad Homburg (DE)

(72) Inventors: Harry Pütter, Bad Salzschlirf (DE); Steffen Baumgart, Hünfeld (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 635 days.

(21) Appl. No.: 16/349,747

(22) PCT Filed: Dec. 12, 2017

(86) PCT No.: PCT/EP2017/082414
§ 371 (c)(1),
(2) Date: May 14, 2019

(87) PCT Pub. No.: WO2018/127366
PCT Pub. Date: Jul. 12, 2018

(65) Prior Publication Data
US 2019/0269898 A1    Sep. 5, 2019

(30) Foreign Application Priority Data

Jan. 9, 2017   (EP) .................................... 17150606

(51) Int. Cl.
*A61M 25/16*    (2006.01)
*A61M 25/18*    (2006.01)
(Continued)

(52) U.S. Cl.
CPC ............ *A61M 39/10* (2013.01); *A61M 39/26* (2013.01); *A61J 15/0026* (2013.01);
(Continued)

(58) Field of Classification Search
CPC ........ A61J 15/0026; A61M 2039/1033; A61M 2039/1072; A61M 2039/267;
(Continued)

(56) References Cited

U.S. PATENT DOCUMENTS 9,933,094 B2 *   4/2018   Fangrow ............... A61M 39/18
2003/0060804 A1 *   3/2003   Vaillancourt ......... A61M 39/14
604/533

(Continued)

FOREIGN PATENT DOCUMENTS

WO    WO 2007/073939 A1    7/2007
WO    WO 2013/036854 A1    3/2013

OTHER PUBLICATIONS

International Search Report and Written Opinion, counterpart International Appl. No. PCT/EP2017/082414 (dated Mar. 6, 2018) (16 pages).

*Primary Examiner* — Rebecca E Eisenberg
(74) *Attorney, Agent, or Firm* — Cook Alex Ltd.

(57) ABSTRACT

A connector assembly for connecting medical lines (3, 4) to each other comprises a first connector (1) having an insertion shaft (12), and a second connector (2) having an insertion opening (22). For connecting the first connector (1) and the second connector (2) to each other, the insertion shaft (12) of the first connector (1) is insertable along an insertion direction (I) into the insertion opening (22) of the second connector (2). For releasing the first connector (1) and the second connector (2) from each other, the insertion shaft (12) of the first connector (1) is removable from the insertion opening (22) of the second connector (2). The first connector (1) comprises an elastic member (14) arranged on the insertion shaft (12), wherein the elastic member (14) comprises an abutment portion (141) abutting a surface (121) of the insertion shaft (12) and being displaceable along the insertion direction (I) relative to the surface (121) of the (Continued)

insertion shaft (12) upon releasing the first connector (1) and the second connector (2) from each other. In this way a connector assembly is provided which, in an easy way, allows for the cleaning of at least the first connector.

11 Claims, 5 Drawing Sheets

(51) Int. Cl.
*A61M 39/00* (2006.01)
*A61M 39/10* (2006.01)
*A61M 39/26* (2006.01)
*A61J 15/00* (2006.01)

(52) U.S. Cl.
CPC ............... *A61M 2039/1033* (2013.01); *A61M 2039/1072* (2013.01); *A61M 2039/267* (2013.01); *A61M 2205/0205* (2013.01); *A61M 2205/0216* (2013.01)

(58) Field of Classification Search
CPC .. A61M 2205/0205; A61M 2205/0216; A61M 39/10; A61M 39/26
See application file for complete search history.

(56) References Cited

U.S. PATENT DOCUMENTS

| | | |
|---|---|---|
| 2004/0171993 A1 | 9/2004 | Bonaldo |
| 2005/0087715 A1* | 4/2005 | Doyle ................. A61M 39/045 251/149.1 |
| 2007/0218757 A1 | 9/2007 | Guala |

* cited by examiner

CONNECTOR ASSEMBLY FOR CONNECTING MEDICAL LINES TO EACH OTHER

The invention relates to a connector assembly for connecting medical lines to each other.

A connector assembly of this kind comprises a first connector having an insertion shaft and a second connector having an insertion opening. For connecting the first connector and the second connector to each other, the insertion shaft of the first connector can be inserted along an insertion direction into the insertion opening of the second connector. In turn, for releasing the first connector and the second connector from each other, the insertion shaft of the first connector is removable from the insertion opening of the second connector. The connectors for example may both comprise a screw thread such that the connectors may be screwed together to form a screw-type connection.

A medical line of this kind may for example be a line used for the enteral feeding of a patient. Enteral feeding generally refers to the delivery of a nutritionally complete feed, containing protein, carbohydrate, fat, water, minerals and vitamins, directly into the stomach, duodenum or jejunum of a patient. A feeding tube, for this purpose, may for example be passed through the nares (nostril), down the esophagus and into the stomach (so-called nasogastric feeding tube). A nasojejunal feeding tube, in comparison, may be passed further through the stomach into the jejunum, the middle section of the small intestine. And a gastric feeding tube is a tube inserted through a small incision in the abdomen into the stomach and is used, preferably, for long-term enteral nutrition.

When using feeding lines for the enteral feeding of a patient, a first line may for example be placed on the patient, for example providing a feeding port to the stomach. This first line may remain on the patient for a rather long time, for example a few days or even a few weeks. Another, second line may be connected to this first line for the actual feeding, wherein for each feeding procedure a new second line may be used and disposed after the feeding procedure.

A connector assembly in this regard serves to connect the feeding lines to each other. A first connector (also denoted as male connector) herein may be arranged for example on the line placed on the patient, whereas a second connector (female connector) may be used on the second line for connecting the second line to the first line for carrying out an actual feeding procedure.

Whereas the second connector may be used only once for carrying out a feeding procedure, the first connector connected to the line placed on the patient may be re-used multiple times. Because the first connector is re-used multiple times for multiple feeding procedures, it is to be made sure that the first connector is clean when connecting the lines to each other, in order to avoid a contamination of any solution passed towards the patient.

Such cleaning, however, may not be easy, because the insertion shaft of the first (male) connector may actually not be easily accessible.

It is an object of the instant invention to provide a connector assembly which, in an easy way, allows for the cleaning of at least the first connector.

This object is achieved by a connector assembly according to the present embodiments.

Accordingly, the first connector comprises an elastic member arranged on the insertion shaft, wherein the elastic member comprises an abutment portion formed to abut a surface of the insertion shaft and being displaceable along the insertion direction relative to the surface of the insertion shaft upon releasing the first connector and the second connector from each other.

Hence, the abutment portion abuts the surface of the insertion shaft. The elastic member is placed on the insertion shaft. The elastic member, by means of an abutment portion, is constituted to contact the surface of the insertion shaft such that it may slide along the surface upon inserting the insertion shaft of the first connector into the associated insertion opening of the second connector for connecting the connectors to each other and, just as well, upon removing the insertion shaft from the insertion opening for releasing the connectors from each other.

The abutment portion may be formed to always abut the (substantially smooth) surface of the insertion shaft. The abutment portion however may also be formed to come into abutment with the surface only upon connecting the connectors to each other (and might for example not abut the surface in a disconnected state of the connectors).

By swiping along the surface of the insertion shaft, the abutment portion of the elastic member provides for a cleaning of the surface of the insertion shaft. Hence, in particular when releasing the connectors from each other, the abutment portion slides along the surface of the insertion shaft and, thus, removes dirt and other residuals from the surface. Upon releasing the connectors from each other, hence, an automatic cleaning of the insertion shaft is provided, wherein after releasing the connectors from each other the elastic member as well as a tip of the insertion shaft may be swabable for removing dirt and residuals from the first connector and for disinfecting the first connector.

The insertion shaft may for example have a cylindrical shape having a circular cross section. The insertion opening of the second connector has a complementary cylindrical shape and hence may receive the insertion shaft upon connecting the connectors to each other.

The elastic member, in particular, may be elastically deformable along the insertion direction. Hence, when inserting the insertion shaft of the first connector into the insertion opening of the second connector, the elastic member is deformed (for example compressed) along the insertion direction and slides, with its abutment portion, along the insertion shaft. In turn, when releasing the connectors from each other, the elastic member resets to its original, expanded state and swipes along the surface of the insertion shaft.

The abutment portion, in one embodiment, may have a ring shape. The abutment portion herein may for example extend circumferentially about the insertion shaft, the ring shaped abutment portion being moved axially along the insertion shaft when connecting the connectors to each other or when releasing the connectors from each other.

The first connector, in one embodiment, comprises a first body circumferentially extending about the insertion shaft such that an inner space is formed radially in between the first body and the insertion shaft. The first body hence is placed at a radial distance to the insertion shaft and is arranged for example coaxially with the insertion shaft. In between the first body and the insertion shaft the radial inner space is formed in which, preferably, the elastic member is received.

When the first connector and the second connector are released from each other and hence are separated from each other, the elastic member may assume an expanded state in which the abutment portion closes the inner space towards the outside. The abutment portion, in this state, may be approached towards the tip of the insertion shaft and, for example by circumferentially extending about the insertion shaft, close the radial inner space such that dirt may not enter into the inner space beyond the abutment portion.

The abutment portion may, in one embodiment, be supported on the bottom of the inner space by means of an elastic portion of the elastic member. The elastic portion may for example be compressed along the insertion direction when connecting the connectors to each other, such that an elastic tensioning is provided which causes the elastic member to reset towards its expanded state upon releasing the connectors from each other.

The connectors may for example be connected to each other by means of a screw connection. Herein, for example on an inner face of the first body a first screw thread may be provided, the first screw thread being engageable with a second screw thread on a second body of the second connector. Hence, for connecting the connectors to each other, the connectors are screwed together, such that the insertion shaft of the first connector is inserted along the insertion direction in the corresponding insertion opening of the second connector.

When the first connector and the second connector are released from each other and hence the first connector is separated from the second connector, the abutment portion of the elastic member may be arranged relative to the insertion shaft such that the surface of the abutment portion is substantially flush with a tip of the insertion shaft. This allows for an easy swabbing of the tip of the connector as well as of the surface of the abutment portion, such that dirt can easily be removed when the connectors are released from each other, wherein in addition a disinfection of the surface of the abutment portion as well as of the tip of the insertion shaft may be achieved by swabbing the tip of the insertion shaft as well as the surface of the abutment portion using a suitable disinfection solution.

In an alternative embodiment the abutment portion may comprise a split septum which, when the first collector is released from the second connector, covers the tip of the insertion shaft towards the outside. The split septum comprises a slit such that, upon connecting the connectors to each other, the septum may be split and the insertion shaft of the first connector may reach through the slit of the septum, the septum hence being deformed and being moved along the surface of the insertion shaft. The split septum, in a disconnected state of the connectors, may comprise for a sealing of the channel opening formed in the insertion shaft, and furthermore may allow for an easy cleaning of the first connector.

The second connector beneficially comprises a second body in which the insertion opening for receiving the insertion shaft of the first connector is formed. On the circumferential outer wall of the second body a second screw thread may be formed and may be engageable with the first screw thread of the first connector for establishing a screw type connection in between the connectors.

The elastic member, in one embodiment, is integrally formed from an elastic material, for example a plastics material such as an elastomer or an elastic foam material.

The connector assembly provides for the connection between lines, for example feeding lines for the enteral feeding. Correspondingly, the first connector may comprise a first connection shaft axially aligned with the insertion shaft for receiving a first connection line, whereas the second connector may comprise a second connection shaft axially aligned with the insertion opening for receiving a second connection line. Hence, connection lines, such as feeding lines, may be connected to the connectors and, via the connectors, may be connected to each other to provide for a liquid transfer between the connection lines.

In one embodiment, at least one of the insertion shaft of the first connector, the elastic member of the first connector, another portion of the first connector and a portion of the second connector comprises antimicrobial characteristics, such as a (rigid or liquid) coating of a antimicrobial substance or the like. An antimicrobial substance is a chemical substance which acts against microorganisms and stops their growth. For example, an antibiotic represents an antimicrobial substance to be used against bacteria, and an antifungal represents an antimicrobial substance to be used against fungi. An antimicrobial may be a substance of natural, semi-synthetic or synthetic origin suitable to act against microorganisms.

The idea underlying the invention shall subsequently be explained in more detail with reference to the embodiments shown in the figures. Herein:

FIG. 1 shows a schematic drawing of a feeding line assembly comprising feeding lines 3, 4 placed on a patient P.

The feeding lines 3, 4 for example serve for providing for an enteral feeding of the patient P. For this, a first line 3 may, for example through an incision in the abdomen of the patient P, be inserted into the stomach of the patient P and may be used as a port for a long-term enteral feeding. A second feeding line 4 is connected to the first feeding line 3 via a connector assembly comprising connectors 3, 4, the second feeding line 4 for example being connected to a container comprising an enteral feeding solution, which via the lines 3, 4 is delivered towards the patient P for example using a suitable pumping device.

Whereas the second feeding line 4 may be used for example only once in connection with the container comprising the enteral feeding solution and may be disposed after use, the feeding line 3 placed on the patient P may remain on the patient P for a rather long term, for example a few days or even a few weeks, and may be used multiple times to carry out multiple feeding procedures. There hence is a necessity to keep the feeding line 3 as well as the connector 1 connected to the feeding line 3 clean, such that a contamination of the feeding line 3 and the connector 1 connected to it is effectively prevented.

Figure 1:
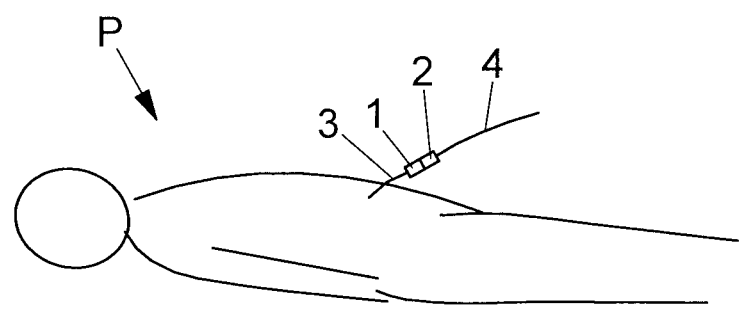
FIG. 1 shows a schematic drawing of a feeding line placed on a patient.
Figure 2:
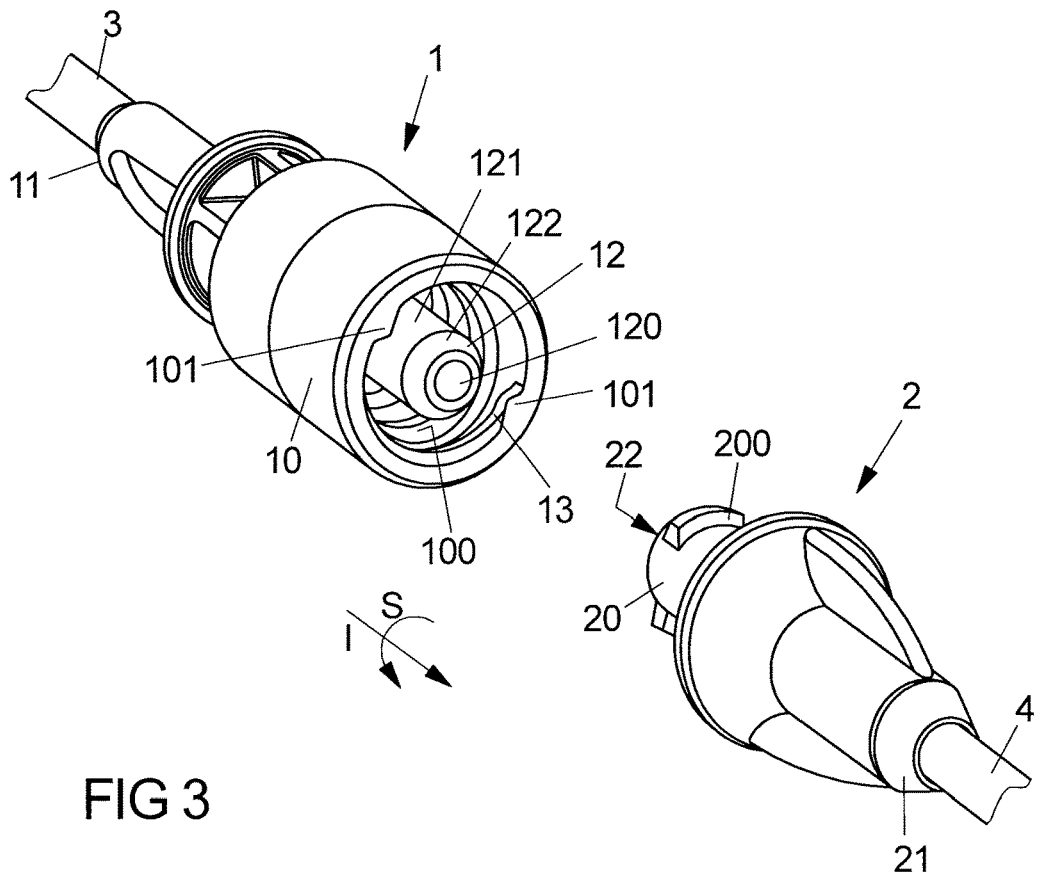
FIG. 2 shows an embodiment of a connector assembly having a first connector and a second connector.

An embodiment of a connector assembly comprising connectors 1, 2 is shown in FIG. 2. The first connector 1 herein may for example be connected to the feeding line 3 placed on the patient P, whereas the second connector 2 is arranged on the other, second feeding line 4 connected to a container comprising a feeding solution.

The first connector 1, in this embodiment, comprises a cylindrical body 10 circumferentially coaxially extending about a cylindrical insertion shaft 12 and forming, together with the insertion shaft 12, a radial inner space 13. On the inner wall of the body 10 a screw thread 100 is arranged allowing for a screw type connection with the second connector 2.

The insertion shaft 12 can be inserted in an insertion direction I into an insertion opening 22 in a body 20 of the second connector 2. On the body 20 of the second connector 2 a screw thread 200 is arranged, such that the second connector 2 can be screwed into the inner space 13 of the first connector 1 by engaging the screw threads 100, 200 with each other and by screwing the first connector 1 along a screwing direction S on the second connector 2.

The insertion shaft 12 has a substantially cylindrical shape having a circular cross section. The insertion opening 22 of the second connector 2 has a corresponding, complementary shape and hence is suited to receive the insertion shaft 12.

When screwing the connectors 1, 2 on to each other, the insertion shaft 12 is inserted into the insertion opening 22. The insertion shaft 12 comprises a channel opening 120, which extends through the insertion shaft 12 and through a shaft 11 aligned with the insertion shaft 12, the shaft 11 being connected to the associated feeding line 3. Likewise, the insertion opening 22 is aligned with a shaft 21 of the second connector 2, the shaft 21 being connected to the feeding line 4. Hence, by connecting the connectors 1, 2 to each other, a fluid connection between the feeding lines 3, 4 can be established, such that a medical fluid such as an enteral feeding solution may pass from the feeding line 4 through the connectors 1, 2 into the feeding line 3.

Figure 3:
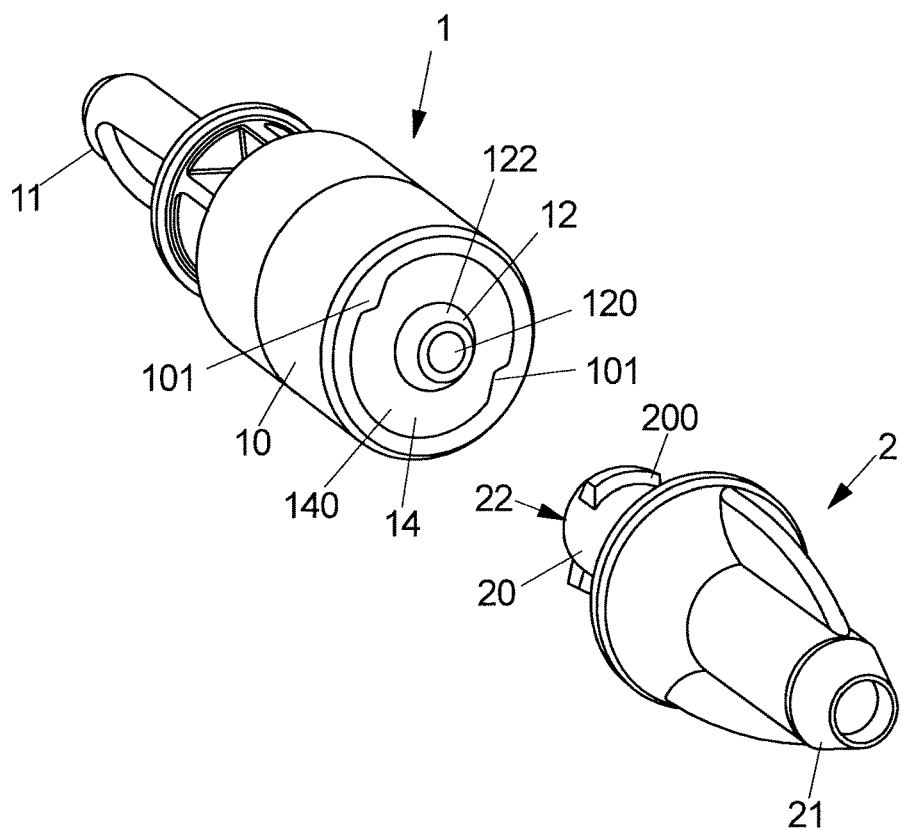
FIG. 3 shows the embodiment of FIG. 2, with an elastic member arranged on the first connector.
Figure 4:
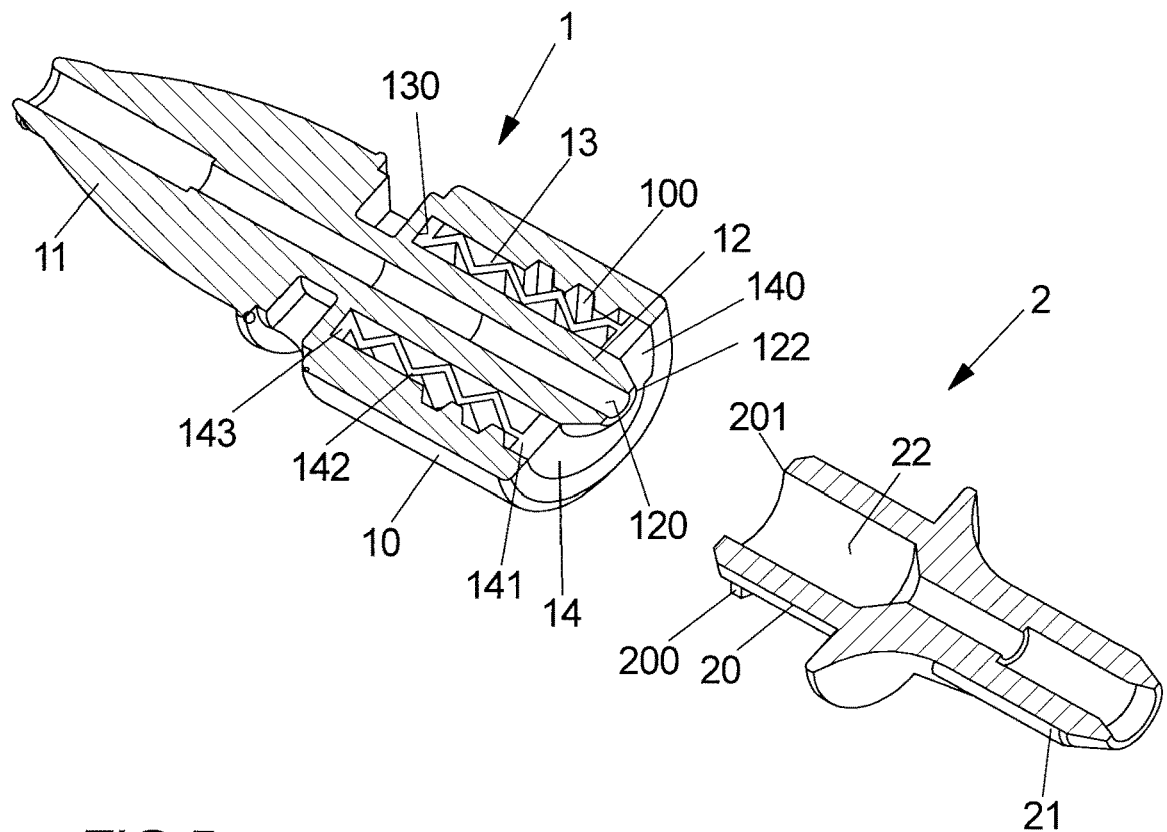
FIG. 4 shows a sectional view of the connector assembly, in a released state of the connectors.
Figure 5:
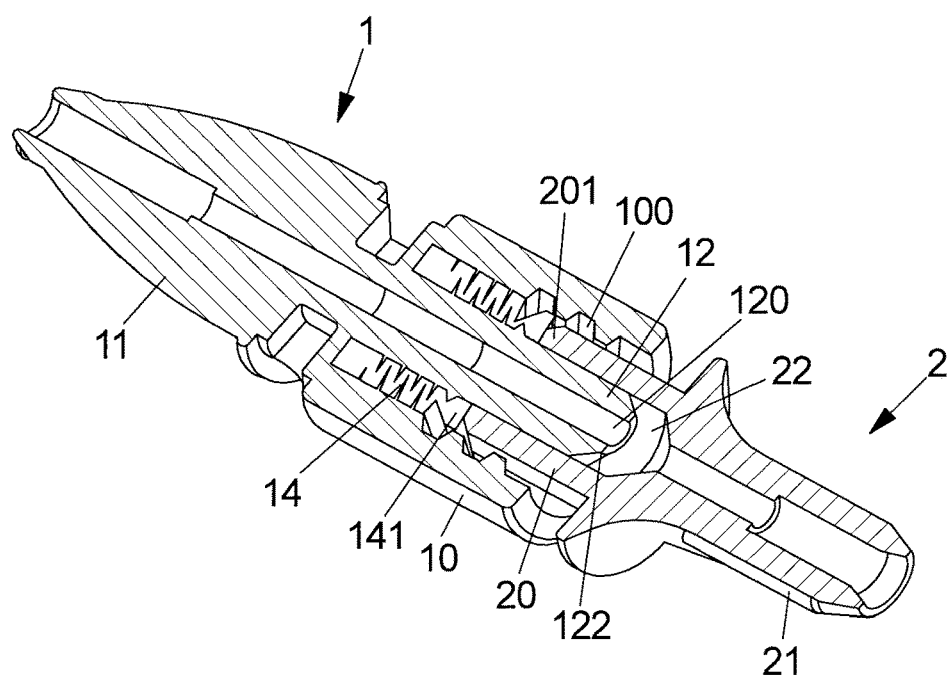
FIG. 5 shows a sectional view of the connector assembly, in a connected state of the connectors.

As shown in an embodiment in FIGS. 3 to 5, within the radial inner space 13 in between the body 10 and the insertion shaft 12 of the first connector 1, an elastic member 14 is arranged, the elastic member 14 comprising a ring-shaped abutment portion 141 surrounding the insertion shaft 12 and being, with its surface 140, substantially flush with the tip 122 of the insertion shaft 12 (pointing towards the second connector 2) when the connectors 1, 2 are separated from each other (see FIGS. 3 and 4). The abutment portion 141 is supported with respect to the bottom 130 of the radial inner space 13 by means of an elastic portion 142 of the elastic member 14, the elastic portion 142 causing the abutment portion 141 to assume the state shown in FIGS. 3 and 4 when the connectors 1, 2 are not connected to each other.

When connecting the connectors 1, 2 to each other, the second connector 2, with a front rim 201 of the body 20, comes into contact with the surface 140 of the abutment portion 141 of the elastic member 14. When the connectors 1, 2 are screwed onto each other such that the insertion shaft 12 is inserted into the associated insertion opening 22 of the second connector 2, the body 20 of the second connector 2 causes the elastic portion 142 of the elastic member 14 to be compressed such that the abutment portion 141 slides along the outer cylindrical surface 121 of the insertion shaft 12 and swipes along the surface 121 along the insertion direction I (see FIG. 5).

When the second connector 2 again is removed from the first connector 1 by unscrewing the connectors 1, 2 from each other, the insertion shaft 12 slides out of engagement of the engagement opening 22, and the body 20 of the second connector 2 exits from the radial inner space 13 in between the body 10 and the insertion shaft 12 of the first connector 1. Due to the elasticity of the elastic portion 142, the elastic member 14 resets to its original, expanded state (FIGS. 3 and 4), causing the abutment portion 141 to slide along the cylindrical circumferential surface 121 of the insertion shaft 12, hence swiping away any residuals on the insertion shaft 12 and hence cleaning the insertion shaft 12 from dirt.

After separating the connectors 1, 2 from each other (see FIG. 3), the tip 122 of the insertion shaft 12 and the surface 140 of the abutment portion 141 of the elastic member 14 are accessible from the outside and may be swabbed using for example a suitable cleaning cloth. Because the surface 140, in the state of FIG. 3, is substantially flush with the tip 122 of the insertion shaft 12, dirt and residuals may easily be removed from the elastic member 14 as well as from the insertion shaft 12. In addition, for example a suitable disinfection for example by using a disinfection solution may be achieved.

In the expanded state shown in FIGS. 3 and 4 the abutment portion 141 of the elastic member 14 abuts on protrusions 101 protruding radially inwards from the body 10, such that the abutment portion 141 assumes a defined axial position with respect to the insertion shaft 12.

The connectors 1, 2 may for example be fabricated from a comparatively hard plastics material, for example by injection molding.

The elastic member 14 may for example be fabricated from an elastic plastics material, for example an elastomer or an elastic foam material.

In particular, the elastic portion 142 of the elastic member 14 is compressible such that by connecting the connectors 1, 2 to each other the elastic portion 142 may be deformed and the abutment portion 141 may be moved into the inner space 13, as it is shown for example in FIG. 5.

Figure 6:
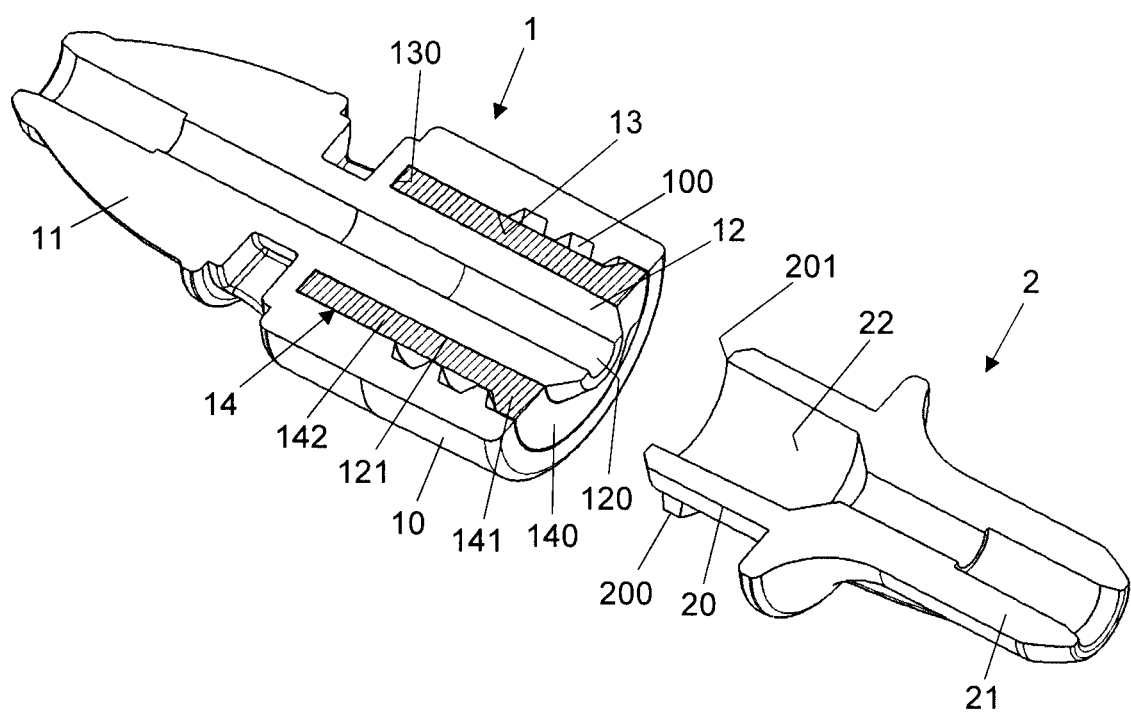
FIG. 6 shows a sectional view of another embodiment of a connector assembly having a first connector and a second connector.

Whereas in the embodiment of FIGS. 3 to 5 the elastic portion 142 of the elastic member 14 is formed (integrally with the abutment portion 142) from an elastic material such as an elastomer and is shaped in a meander-like fashion to be compressible along the insertion direction I, in the embodiment of FIG. 6 the elastic member 14 is integrally formed from a compressible foam material such that the elastic member 14 and in particular the elastic portion 142 arranged in the inner space 13 in between the insertion shaft 12 and the body 10 is elastically compressible along the insertion direction I upon inserting the insertion shaft 12 of the first connector 1 into the insertion opening 22 confined by the body 20 of the second connector 2. In this way the abutment portion 141 slides along the outer surface 121 of the insertion shaft 12, hence swiping away any residuals on the insertion shaft 12 and hence cleaning the insertion shaft 12 from dirt, as it has been described above.

Upon removing the connectors 1, 2 from each other the elastic deformation of the elastic portion 142 formed from the elastically compressible foam causes a resetting of the abutment portion 141 to its original position shown in FIG. 6. In a disconnected state of the connectors 1, 2 the surface 140 of the elastic member 14 hence is substantially flush with the tip 122 of the insertion shaft 12 such that the surface 140 and the tip 122 may easily be cleaned.

Figure 7:
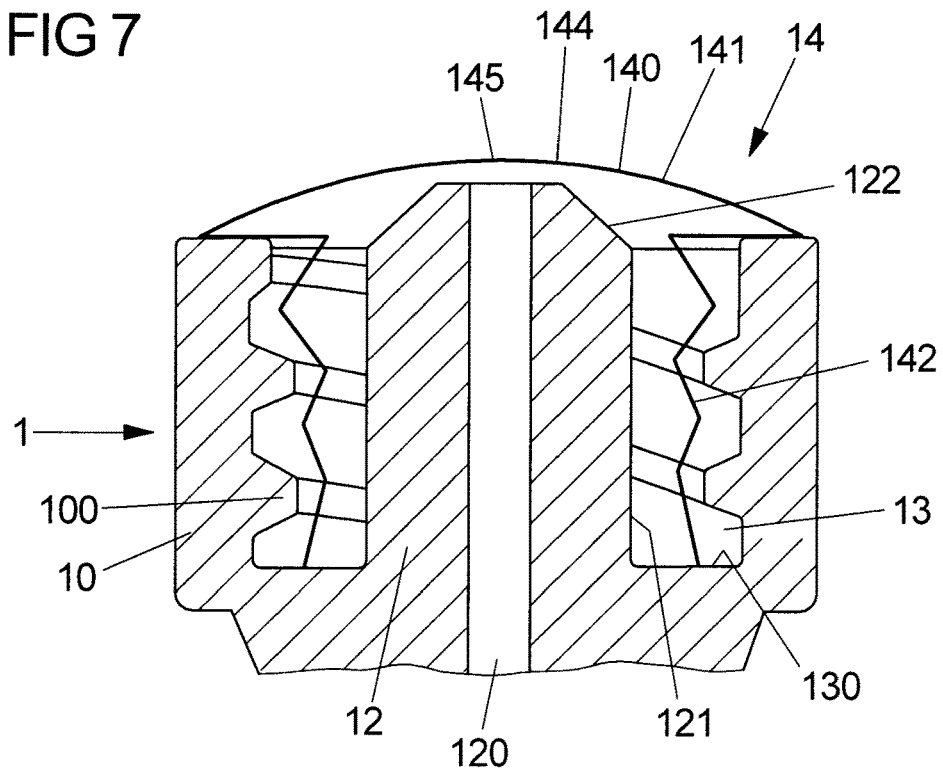
FIG. 7 shows a sectional view of yet another embodiment of a connector assembly.
Figure 8:
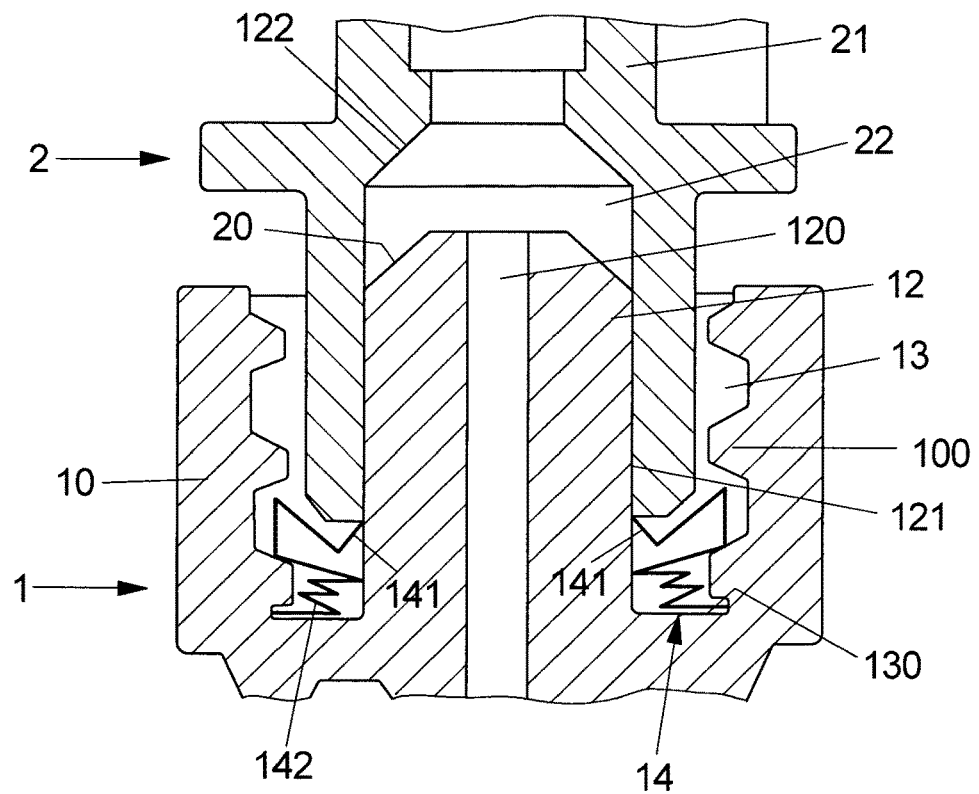
FIG. 8 shows the connector assembly of FIG. 7 in a connected state of the connectors.

FIGS. 7 and 8 show yet another embodiment of a connector assembly having connectors 1, 2 being substantially identical in shape and function as it has been described above.

In contrast to the afore-described embodiments, in the embodiment of FIGS. 7 and 8 the first connector 1 has an elastic member 14 having an abutment portion 141 formed by a split septum 144 covering, in a disconnected state of the connectors 1, 2 as shown in FIG. 7, the tip 122 of the insertion shaft 12 of the first connector 1. In its original, non-deformed state the elastic member 14 hence, in a cap-like fashion, provides for a covering of the insertion shaft 12 and the channel opening 120 formed in the insertion shaft 12, such that the insertion shaft 12 with its channel opening 120 is sealed towards the outside. Herein, the surface 140 of the split septum 144 facing towards the outside is easily cleanable by swabbing using a suitable swabbing cloth. In addition, an easy disinfection by applying a suitable disinfection solution is possible.

An elastic portion 142 extends from the split septum 144 forming the abutment portion 141 and reaches into the space 13 formed in between the insertion shaft 12 and the body 10 of the first connector 1.

The split septum 144 comprises a slit 145 at which the septum 144 may be split. The split septum 144 hence, upon connecting the connectors 1, 2 to each other, may be deformed such that the split septum 144 (forming the abutment portion 141) is moved along the insertion shaft 12 into the radial inner space 13 formed in between the insertion shaft 12 and the body 10 of the first connector 1, as this is shown in FIG. 8. The split septum 144 hence is pressed into the inner space 13, the edges of the slit 145 closely and resiliently abutting the circumferential outer surface 121 of the insertion shaft 12, thus providing for a swiping away of any residuals on the insertion shaft 12 and hence a cleaning of the insertion shaft 12 from dirt.

In a connected state, as shown in FIG. 8, the insertion shaft 12 reaches through the split septum 144 forming the abutment portion 141, and the connectors 1, 2 are connected to each other.

When removing the connectors 1, 2 from each other, the split septum 144 is reset to its original, non-deformed state of FIG. 7 by resetting forces of the elastic portion 142, which cause the split septum 144 (forming the abutment portion 141) to be moved along the circumferential outer surface 121 of the insertion shaft 12 towards the original state of FIG. 7. By this movement again a cleaning of the surface 121 of the insertion shaft 12 is provided, and residuals are removed from the insertion shaft 12.

Once the split septum 144 forming the abutment portion 141 has reached its original state according to FIG. 7, the insertion shaft 12 and the channel opening 120 formed therein are resealed, hence effectively preventing a contamination.

The invention is not limited to the embodiments described above, but may be implemented in an entirely different fashion.

For example, a connector assembly of the kind described herein may not only be used for the enteral feeding, but may be used for connecting any medical lines to each other for transferring medical solutions, such as medication, nutritional solutions, saline solutions or any other solutions.

LIST OF REFERENCE NUMERALS

1 Connector (male part)
10 Body
100 Screw thread
101 Protrusion
11 Shaft
12 Insertion shaft
120 Channel opening
121 Surface (outer wall)
122 Tip
13 Space
130 Bottom
14 Elastic member
140 Surface
141 Abutment portion (ring body)
142 Elastic portion
143 Bottom part
144 Split septum
145 Slit
2 Connector (female part)
20 Body
200 Screw thread
201 Front rim
21 Shaft
22 Insertion opening
3 Line
4 Line
I Insertion direction
P Patient
S Screwing direction

The invention claimed is:

1. A connector assembly for connecting medical lines to each other, comprising:
a male first connector having an insertion shaft, and
a female second connector having an insertion opening,
wherein, for connecting the male first connector and the female second connector to each other, the insertion shaft of the male first connector is insertable along an insertion direction into the insertion opening of the female second connector and, for releasing the male first connector and the female second connector from each other, the insertion shaft of the male first connector is removable from the insertion opening of the female second connector,
wherein
the male first connector comprises an elastic member arranged on the insertion shaft, the elastic member comprising an abutment portion formed to abut a surface of the insertion shaft, and being displaceable along the insertion direction relative to the surface of the insertion shaft upon releasing the male first connector and the female second connector from each other such that the abutment portion of the elastic member of the male first connector slides along the surface of the insertion shaft, wherein the abutment portion comprises a surface which is substantially flush with a tip of the insertion shaft when the male first connector is released from the female second connector,
wherein the male first connector comprises a first body circumferentially extending about the insertion shaft such that an inner space is formed radially in between the first body and the insertion shaft, the elastic member being received in the inner space, and
wherein the abutment portion of the elastic member closes the inner space towards the outside when the male first connector is released from the female second connector.

2. The connector assembly according to claim 1, wherein the insertion shaft has a cylindrical shape.

3. The connector assembly according to claim 1 wherein the elastic member is elastically deformable along the insertion direction.

4. The connector assembly according to claim 1 wherein the abutment portion has a ring shape and extends circumferentially about the insertion shaft.

5. The connector assembly according to claim 1 wherein the elastic member comprises an elastic portion elastically supporting the abutment portion on a bottom of the inner space.

6. The connector assembly according to claim 1 wherein the first body comprises a first screw thread for connecting the male first connector and the female second connector to each other.

7. The connector assembly according to claim 1 wherein the female second connector comprises a second body in which the insertion opening is formed.

8. The connector assembly according to claim 7, wherein the second body comprises a second screw thread for connecting the male first connector and the female second connector to each other.

9. The connector assembly according to claim 1 wherein the elastic member is integrally formed from a plastics material.

10. The connector assembly according to claim 1 wherein the male first connector comprises a first connection shaft axially aligned with the insertion shaft for receiving a first connection line.

11. The connector assembly according to claim 1 wherein the female second connector comprises a second connection shaft axially aligned with the insertion opening for receiving a second connection line.

* * * * *